United States Patent [19]
Goldstein et al.

[11] Patent Number: 5,639,729
[45] Date of Patent: Jun. 17, 1997

[54] TRIPEPTIDES USEFUL IN IMMUNE AND CNS THERAPY

[75] Inventors: Gideon Goldstein, Short Hills; Ponniah Shenbagamurthi, Bridgewater; James I. Koenig, Glen Gardner, all of N.J.

[73] Assignee: Immunobiology Research Institute, Inc., Annandale, N.J.

[21] Appl. No.: 112,413

[22] Filed: Aug. 26, 1993

[51] Int. Cl.$^6$ .......................... A61K 38/00; A61K 38/02; C07K 5/00; C07K 7/00
[52] U.S. Cl. .............................................. 514/18; 530/331
[58] Field of Search .............................. 530/331; 514/18

[56] References Cited

U.S. PATENT DOCUMENTS

| | | | |
|---|---|---|---|
| 4,190,646 | 2/1980 | Goldstein et al. | 424/177 |
| 4,505,853 | 3/1985 | Goldstein et al. | 260/112.5 R |
| 4,629,723 | 12/1986 | Goldstein et al. | 514/17 |
| 5,013,723 | 5/1991 | Sisto et al. | 514/19 |
| 5,028,592 | 7/1991 | Lipton | 514/18 |

FOREIGN PATENT DOCUMENTS

| | | |
|---|---|---|
| 166612 | 6/1985 | European Pat. Off. . |
| 146266 | 1/1986 | European Pat. Off. . |
| 342962 | 11/1989 | European Pat. Off. . |
| 361977 | 4/1990 | European Pat. Off. . |
| 410372 | 1/1991 | European Pat. Off. . |
| US89/01967 | 11/1989 | WIPO . |
| US89/04000 | 4/1990 | WIPO . |

OTHER PUBLICATIONS

Websters II Dictionary p. 1230.

R. Merrifield, "Solid Phase Peptide Synthesis. I. The Synthesis of a Tetrapeptide", *J. Amer. Chem. Soc.*, 85:2149-2154 (Jul. 20, 1963).

T. Wieland, "Solution vs. Solid-Phase Methods in Peptide Chemistry", in *Techniques in protein Chemistry*, pp. 59-80, by Academic Press, Inc., New York (1978).

T. Audhya et al, "Isolation and Complete Amino Acid Sequence of Human Thymopoetin and Splenin", *Proc. Natl. Acad. Sci. USA*, 84:3545-3549 (1987).

G. Heavner et al, "Peptide Analogs of Thymopentin Distinguish Distinct Thymopoietin Receptor Specificities on Two Human T Cell Lines", *Regulatory Peptides*, 27:257-262 (1990) [Heavner I].

G. Chipens et al, "Localization and Steric Structure of Active Sites and Fragments of Ig Molecules", in *LPSR Zinatnu Akademija*, (198 ) [Chipens I].

G. Chipens et al, "Synthesis of Immunoproteins: New Biologically Active Low-Molecular Weight Fragments of Immunoglobulins", *Bioorganicheskaya Kimiya*, 11(4):437-446 (1985) [Chipens II].

G. Heavner et al, "Biologically Active Analogs of Thymopentin with Enhanced Enzymatic Stability", *Peptides*, 7:1015-1019 (1986) [Heavner II].

R. H. Brown et al, "Immunoreactive Thymopoietin in the Mouse Central Nervous System", *Brain Research*, 381:237-243 (1986).

K. Venkatasubramanian et al, "Binding of Thymopoietin to the Acetylcholine Receptor", *Proc. Natl. Acad. Sci. USA*, 83:3171-3174 (1986).

M. Quik et al, "Evidence for Thymopoietin and Thymopoietin/ α-Bungarotoxin/Nicotinic Receptors within the Brain", *Proc. Natl. Acad. Sci. USA*, 88:2603-2607 (1991) [Quik I].

M. Quik et al, "Thymopoietin and Thymic Polypeptide, Specifically Interacts at Neuronal Nicotinic α-Bungarotoxin Receptors", *J. Neurochem.*, 53(4):1320-1323 (1989) [Quik II].

F. Revah et al, "Calcium-Dependent Effect of the Thymic Polypeptide Thymopoietin on the Desensitization of the Nicotinic Acetylcholine Receptor" *Proc. Natl. Acad Sci USA*, 84:3477-3481 (1987).

M. Quik et al, "Thymopoietin Inhibits Function and Ligand Binding to Nicotinic Receptors at the Neuromuscular Junction", *J. Pharm. and Exp. Therap.*, 254(3):1113-1119 (1990) [Quik III].

M. Weksler et al, "Immunological Studies of Aging IV. The Contribution of Thymic Involution to the Immune Deficiencies of Aging Mice and Reversal with Thymopoietin", *J. Exp. Med.*, 148: 996-1006 (1978).

E. Sundal et al, "Therapy with Thymopentin: A Clinical Overview", Immune Regulation by Characterized Polypeptides, pp. 121-136 (1987).

Merrifield, "Solid Phase Synthesis", *Angew. Chem. Int.* (ed. Engl.), 24:799-892.

Rajnavogyi et al, "The Influence of New Thymopoietin Derivatives in the Immune Response of Inbred Mice", *Chem. Abst.*, 105:74, Abstract No. 105:800X (1986).

Kassai Tanczos et al, "Submolecular Acid-Base Properties of Bioligands. III. Microspeciation of Thymopoietin-type Tetrapeptides and their Derivatives", *Chem. Abst.*, 115:1053, Abstract No. 136769h (1991).

B. Noszal et al, "Acid-Base Properties of Thymopoietin-type Tri- and Tetrapeptides and their Derivatives", *Chem. Abst.*, 115[:]992, Abstract No. 183935u (1991).

H. Kalbacher et al, "Acid Labile Protection of Histidine and Arginine in SPPS using Adpoc Derivatives", *Chem. Abst.*, 115:1079, Abstract No. 208510s (1991).

V. Klusa et al, "Thymopentin Antagonizes Stress-Induced Changes of GABA/Benzodiazepine Receptor Complex", *Regulatory Peptides*, 27:355-365 (1990).

G. Chipens et al, "Localization and Steric Structure of Active Sites and Fragments of Ig Molecules", in *LPSR Zinatnu Akademija* (1984) [Chipens I].

A. Costa et al, "Effects of Etoperidone on Sympathetic and Pituitary-Adrenal Responses to Diverse Stressors in Humans", *Clin. Neuropharm.*, 16(2):127-138 (1993).

E. Merlo-Pich et al, "Blockade of Pituitary-Adrenal Axis Activation Induced by Peripheral Immunoneutralization of Corticotropin-Releasing Factor does not Affect the Behavioral Response to Social Defeat Stress in Rats", *Psychoneuroendocrinology*, 18(7):495-507 (1993).

S Pellow et al, "Validation of Open:Closed Arm Entries in an Elevated Plus-Maze as a Measure of Anxiety in the Rat", *J. Neurosci. Meth.*, 14:149-167 (1985) [Pellow I].

S. Pellow et al, "Anxiolytic and Anxiogenic Drug Effects on Exploratory Activity in an Elevated Plus-Maze: a Novel Test of Anxiety in the Rat", *Pharmacol. Biochem. Behavior*, 24:525-529 (1986) [Pellow II].

D. Ramsay, "Effects of Circulating Angiotensin II on the Brain", *Frontiers in Neuroendocrinology*, 7:263-285 (1982).

*Primary Examiner*—Christina Y. Chan
*Assistant Examiner*—A. M. Davenport
*Attorney, Agent, or Firm*—Howson and Howson

[57] ABSTRACT

Tripeptides capable of regulating the function of cells of the mammalian immune and/or central nervous system, pharmaceutical compositions containing the peptides and methods of use thereof are provided.

3 Claims, 1 Drawing Sheet

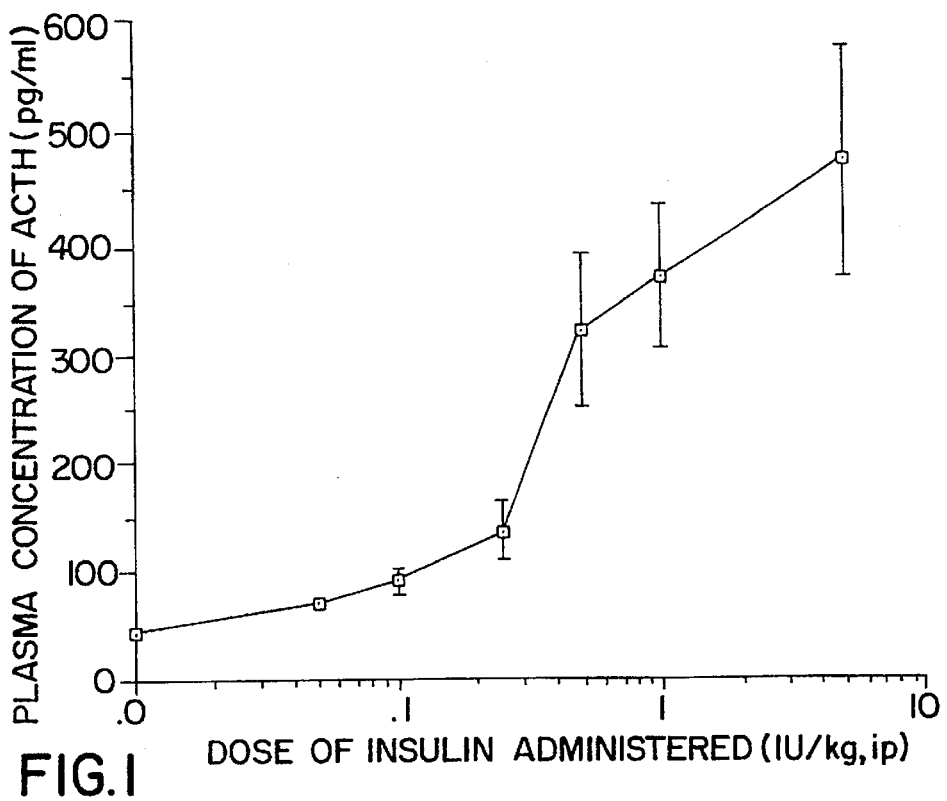
FIG. I
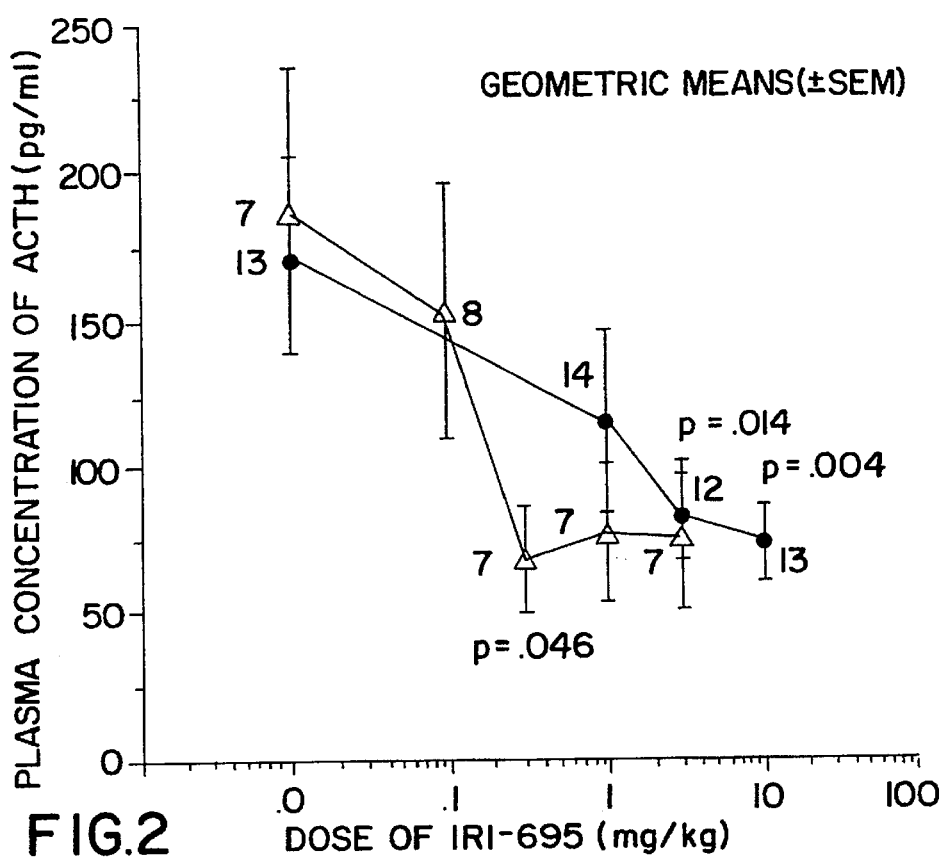
FIG. 2

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 5 amino acids
( B ) TYPE: amino acid
( D ) TOPOLOGY: unknown ( i i ) MOLECULE TYPE: peptide ( x i ) SEQUENCE DESCRIPTION: SEQ ID NO:1:

Arg Lys Asp Val Tyr
1               5

TRIPEPTIDES USEFUL IN IMMUNE AND CNS THERAPY

FIELD OF THE INVENTION

This application relates generally to the field of peptides useful in immune and central nervous system therapy, and more specifically to novel peptides which are biologically active.

BACKGROUND OF THE INVENTION

The immunomodulatory protein thymopoietin has been isolated from bovine and human thymus. Additionally, small peptides have been chemically synthesized which mimic the biological activity of thymopoietin. See, e.g. U.S. Pat. No. 4,505,853 and corresponding EP application No. 146,266.

A large body of articles and patents have now been published relating to such proteins and synthesized peptides. U.S. Pat. No. 4,190,646 discloses the pentapeptide thymopentin which is the active site of thymopoietin and has the sequence Arg-Lys-Asp-Val-Tyr SEQ ID NO: 1, as well as peptide compositions in which various groups are substituted onto the amino and/or carboxyl termini of this pentapeptide.

Thymopoietin is known to regulate cholinergic neuromuscular transmission [G. Goldstein and W. W. Hoffman, *J. Neurol. Neurosurg. Psychiatry*, 31:453–459 (1968); and G. Goldstein, *Nature*, 247:11–14 (1974)]. Thymopoietin is present within the brain, as are thymopoietin receptors (TPR), so that thymopoietin is almost certainly involved in brain function.

More recently, thymopentin has been identified as an antagonist of stress-induced changes, exhibiting stress-protective activity [V. Klusa et al, *Regulatory Peptides*, 27:355–365 (1990)].

There remains a need in the art for additional peptides useful as diagnostic agents and/or therapeutic agents useful in treating dysfunctions of the immune system in humans and other mammals, including those associated with aging and various physical conditions, as well as peptides useful for treating disorders in central nervous system functions.

SUMMARY OF THE INVENTION

The present invention provides novel tripeptides which are biologically active and useful as diagnostics and for treating immune and central nervous system disorders. These peptides are particularly stable and well absorbed and thus are active by the oral route of administration.

Thus, in one aspect, the present invention provides novel peptides of the formula R-Arg-Y-Z-$R_1$, where R, Y, Z, and $R_1$ are as defined below in the detailed description. These peptides are useful in regulating the immune and/or central nervous systems.

As another aspect, the present invention provides methods for preparing the above-described peptides by solution synthesis, solid-phase synthesis or enzymatic synthesis.

In yet another aspect, the present invention provides pharmaceutical compositions comprising one or more of the above-identified peptides in combination with a pharmaceutically acceptable carrier.

Still a further aspect of the present invention provides methods for treating a variety of disorders and deficiencies related to the immune system, in particular, the effects of aging caused by the shrinkage of the thymus gland over time. The present invention also provides methods for treating disorders of the central nervous system, including psychiatric disorders such as anxiety and depression, as well as chronic infections, immune deficiencies and stress. These methods comprise administering an effective amount of a pharmaceutical composition of this invention to an affected subject.

Other aspects and advantages of the present invention are disclosed in the following detailed description containing examples of presently preferred embodiments.

BRIEF DESCRIPTION OF THE DRAWINGS

FIG. 1 is a graph demonstrating the effect of insulin-induced hypoglycemia on plasma ACTH concentrations (pg/ml) in rats (Y ordinate). The X ordinate is the dose of insulin administered intraperitoneally (IU/kg).

FIG. 2 is a graph demonstrating the effects of a peptide of this invention, Acetyl-Arg-Pro-Asp-NH-isobutyl on insulin-induced ACTH secretion, specifically comparing oral dosing (circle) vs. subcutaneous dosing (triangle). The Y ordinate is insulin induced ACTH in plasma (pg/ml) and the X ordinate is dose of peptide (mg/kg).

DETAILED DESCRIPTION OF THE INVENTION

The present invention provides a peptide of the formula $$R\text{-Arg-Y-Z-NHR}_1,$$

where

R is H, lower alkyl or lower alkanoyl;

Y is a D or L form of Pro, dehydro-Pro, or hydroxy-Pro;

Z is a D or L form of an amino acid selected from Ala, Thr, Ser, Asp, Glu, Gln, Asn, beta-Asp, Val or Ile; and $R_1$ is selected from the group consisting of a straight chain or branched alkyl or alkenyl having 1 to 6 carbon atoms, optionally substituted with an aryl group or aryl substituted with either a halogen or a straight chain, a branched alkyl or alkenyl having 1 to 6 carbon atoms, or a cyclic methylene group of 3 to 7 carbon atoms. The Arg can also be present in the D or L form.

Surprisingly, the inventors have discovered that these tripeptides containing substituted amide groups behave in a manner similar to thymopentin peptide analogs which are four or five amino acids in length. Thus, the tripeptides of the invention are capable of regulating and affecting the mammalian immune system. They may also regulate the central nervous system.

Particularly preferred, are the following peptides:

Acetyl-Arg-Pro-Asp-isobutylamide,
Acetyl-Arg-Pro-Thr-isobutylamide,
Acetyl-Arg-Pro-Ser-isobutylamide,
Acetyl-Arg-Pro-Ala-isobutylamide,
Hexanoyl-Arg-Pro-Asp-isobutylamide,
Arg-Pro-Asp-methylamide,
Arg-Pro-Glu-isopropylamide,
Acetyl-Arg-Pro-Asp-methylamide,
Acetyl-Arg-Pro-Asp-isopropylamide,
Acetyl-Arg-Pro-Asp-phenylethylamide,
Formyl-Arg-Pro-Asp-methylamide, and
Hexanoyl-Arg-Pro-Asp-methylamide.

Throughout this disclosure, the amino acid components of the peptides and certain materials used in their preparation are identified by abbreviations for convenience. Most of the three letter abbreviations for amino acids are well known. As defined herein, a lower alkyl is defined as an alkyl having 1 to 10 carbon atoms ($C_1$–$C_{10}$), i.e. a compound of the general formula $C_nH_{2n+1}$, where n is between 1 to 10. Similarly, a lower alkanoyl as defined herein as an alkanoyl having between 1 to 10 carbon atoms, i.e. a compound of the general formula

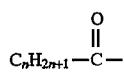

where n is between 0 to 9.

The peptides of this invention may generally be prepared following known techniques. Conveniently, synthetic production of the polypeptide of the invention may be according to the solid phase synthetic method described by Merrifield in *J.A.C.S*, 85:2149-2154 (1963). This technique is well understood and is a common method for preparation of peptides. The solid phase method of synthesis involves the stepwise addition of protected amino acids to a growing peptide chain which is bound by covalent bonds to a solid resin particle. By this procedure, reagents and by-products are removed by filtration, thus eliminating the necessity of purifying intermediates. The general concept of this method depends on attachment of the first amino acid of the chain to a solid polymer by a covalent bond. Succeeding protected amino acids are added, one at a time (stepwise strategy), or in blocks (segment strategy), until the desired sequence is assembled. Finally, the protected peptide is removed from the solid resin support and the protecting groups are cleaved off.

The amino acids may be attached to any suitable polymer as a resin. The resin must contain a functional group to which the first protected amino acid can be firmly linked by a covalent bond. Various polymers are suitable for this purpose, such as cellulose, polyvinyl alcohol, polymethylmethacrylate, and polystyrene. Suitable resins are commercially available and well known to those of skill in the art. Appropriate protective groups usable in such synthesis include t-butyloxycarbonyl (Boc), benzyl (Bzl), t-amyloxycarbonyl (Aoc), tosyl (Tos), o-bromophenylmethoxycarbonyl (BrZ), 2,6-dichlorobenzyl ($BzlCl_2$), and phenylmethoxycarbonyl (Z or CBZ). Additional protective groups are identified in Merrifield, cited above, as well as in J. F. W. McOmie, "Protective Groups in Organic Chemistry", Plenum Press, New York, 1973. Both of these texts are incorporated herein by reference.

The general procedure of preparation of the peptides of this invention involves initially attaching the protected carboxyl-terminal amino acid to the resin. After attachment the resin is filtered, washed and the protecting group (desirably t-butyloxycarbonyl) on the alpha amino group of the carboxyl-terminal amino acid is removed. The removal of this protecting group must take place, of course, without breaking the bond between that amino acid and the resin. The next amino, and if necessary, side chain protected amino acid, is then coupled to the free α-amino group of the amino acid on the resin. This coupling takes place by the formation of an amide bond between the free carboxyl group of the second amino acid and the amino group of the first amino acid attached to the resin. This sequence of events is repeated with successive amino acids until all amino acids are attached to the resin. Finally, the protected peptide is cleaved from the resin and the protecting groups removed to reveal the desired peptide. The cleavage techniques used to separate the peptide from the resin and to remove the protecting groups depend upon the selection of resin and protecting groups and are known to those familiar with the art of peptide synthesis.

Alternative techniques for peptide synthesis are described in Bodanszky et al, *Peptide Synthesis*, 2nd edition (John Wiley and Sons: 1976). For example, the peptides of the invention may also be synthesized using standard solution peptide synthesis methodologies, involving either stepwise or block coupling of amino acids or peptide fragments using chemical or enzymatic methods of amide bond formation. [See, e.g. H. D. Jakubke in *The Peptides, Analysis, Synthesis, Biology*, Academic Press (New York 1987), p. 103–165; J. D. Glass, ibid., pp. 167–184; and European Patent 0324659 A2, describing enzymatic peptide synthesis methods.] These solution synthesis methods are well known in the art.

The peptides of this invention may also be produced by other techniques known to those of skill in the art, for example, genetic engineering techniques. See, e.g., Sambrook et al, in *Molecular Cloning, a Laboratory Manual*, 2nd edition, Cold Spring Harbor Laboratory, Cold Spring Harbor, N.Y. (1989).

The acid- or base-addition salts of these peptides are also disclosed by this invention for use as diagnostic and/or therapeutic agents. Acids which are able to form salts with these peptides include, but are not limited to, inorganic acids, such as hydrochloric acid, hydrobromic acid, perchloric acid, nitric acid, thiocyanic acid, sulfuric acid, phosphoric acid, and the like. Organic acids may also be employed to form the salts of the invention, e.g., formic acid, acetic acid, propionic acid, glycolic acid, lactic acid, pyruvic acid, oxalic acid, malonic acid, succinic acid, maleic acid, fumaric acid, citric acid, succinamic acid, anthranilic acid, cinnamic acid, naphthalene sulfonic acid, sulfanilic acid, and the like.

A nonexclusive list of bases which are able to form salts with those peptides having acidic moieties includes inorganic bases, such as sodium hydroxide, ammonium hydroxide, potassium hydroxide, and the like. Organic bases for such use include, without limitation thereto, mono-, di-, and tri-alkyl and aryl amines (e.g., triethylamine, diisopropylamine, methylamine, dimethylamine) and optionally substituted ethanolamines (e.g., ethanolamine, diethanolamine).

These peptides and compositions containing these peptides surprisingly demonstrate a variety of regulatory effects on the mammalian immune and/or central nervous system. For example, peptides of this invention offer treatment therapies for autoimmune disorders, as well as other conditions characterized by a disorder of the immune system. Because of the immunomodulatory characteristics of the subject peptides, they are therapeutically useful in the treatment of humans, and possibly other animals, since they are capable of effecting changes in the immune system of the mammal.

The peptides of the invention may also be useful as anxiolytic therapeutic agents. For example, pretreatment of a patient with a peptide of the invention may reduce the levels of corticotropin releasing factor (CRF), which mediates stress reactions. Thus, such peptides are useful as anti-depressive treatments, and similarly useful in treatment of other stress-induced disorders.

Also, the peptides according to the present invention may be used to diminish the effects of aging on the immune system. As the thymus shrinks with age, the level of thymopoietin, which is a thymus-derived polypeptide, decreases, and as a result stress-induced levels of CRF, adrenocorticotropic hormone (ACTH) and corticosteroids increase proportionally. Thus, administration of peptides of this invention which have biological activity similar to thymopoietin can help reduce the effects of aging related to inefficient or non-functioning immune systems.

These peptides may also be useful as immunostimulators when administered to a patient having a chronic infection or a deficiency in the immune system. Immune deficiencies can be due to cancer or its treatment, the results of viral infections including HIV and Herpes simplex, among others.

Additionally, the peptides are useful in treating stress during major surgery or stress associated with other trauma, e.g., burns.

The invention further provides pharmaceutical compositions containing one or more of the above-described peptides or acid- or base-addition salts thereof. The subject peptides or pharmaceutical compositions containing the peptides or their acid or base salts are generally considered to be useful in any area in which cellular immunity is an issue and particularly where there are deficiencies in immunity. The pharmaceutical compositions of the invention are also useful in regulating imbalances of the central nervous system.

The invention provides a method for treatment of conditions resulting from disorder of the immune system and/or central nervous system of a subject, which comprises administering to said subject a therapeutically-effective amount of at least one of the peptides or pharmaceutical compositions of this invention. As used herein, the term "therapeutically-effective amount" means an amount which is effective to treat the conditions referred to above.

To prepare the pharmaceutical compositions of the present invention, a peptide of this invention is combined as the active ingredient in intimate admixture with a pharmaceutical carrier according to conventional pharmaceutical compounding techniques. This carrier may take a wide variety of forms depending on the form of preparation desired for administration, e.g., oral, sublingual, rectal, nasal, or parenteral. Currently, the preferred formulation is oral.

In preparing the compositions in the preferred oral dosage form, any of the usual pharmaceutical media may be employed. For oral liquid preparations (e.g., suspensions, elixirs, and solutions), media containing, for example, water, oils, alcohols, flavoring agents, preservatives, coloring agents and the like may be used. Carriers such as starches, sugars, diluents, granulating agents, lubricants, binders, disintegrating agents, and the like may be used to prepare oral solids (e.g., powders, capsules, and tablets). Controlled release forms may also be used. Because of their ease in administration, tablets and capsules represent the most advantageous oral dosage unit form, in which case solid pharmaceutical carriers are obviously employed. If desired, tablets may be sugar coated or enteric coated by standard techniques.

For parenteral products the carrier will usually comprise sterile water, although other ingredients may be included, e.g., to aid solubility or for preservation purposes. Injectable suspensions may also be prepared, in which case appropriate liquid carriers, suspending agents, and the like may be employed.

A tripeptide of the present invention is generally effective when parenterally administered in amounts above about 0.03 mg/kg of body weight to about 30 mg/kg body weight. A preferred amount is about 0.3 mg/kg. When orally administered, the peptides of the present invention are generally active in amounts of between about 0.5 mg/kg of body weight to about 50 mg/kg of body weight. A preferred amount is about 3 mg/kg. Activity at this level makes these peptides particularly well adapted for pharmaceutical formulations in tablet size for oral administration. The above dosages are likely to be administered at varying periods for humans, for example, from daily administration to administration at least twice a week. The presently preferred dosage periodicity is three times per week. However, ultimately, the dosage regimen will depend upon the physical status of the patient and duration of the condition treated, e.g., for viral diseases, the regimen will be selected for the duration of the ailment. For chronic disorders, e.g., stress, HIV, and the like, the regimen will depend on the duration of the symptoms.

The following examples are presented to illustrate the invention without specifically limiting the invention thereto. In the examples and throughout the specification, parts are by weight unless otherwise indicated. In addition to the abbreviations described above, the examples employ the following abbreviations: TFA for trifluoroacetic acid; HOAc for acetic acid; $CH_2Cl_2$ for methylene chloride; $CH_3CN$ for acetonitrile; DMF for dimethyl formamide; $NH_4OAc$ for ammonium acetate; $NH_4OH$ for ammonium hydroxide; n-PrOH for n-propanol; n-BuOH for n-butanol; Pyr for pyridine; DCC for dicyclohexylcarbodiimide; HOBt for 1-hydroxy- benzotriazole; DMAP for dimethylaminopyridine; HF for hydrogen fluoride; TCA for trichloroacetic acid; BHA for benzhydrylamine; p-MBHA for p-methylbenzhydrylamine; DIC for diisopropylcarbodiimide, NMM for N-methylmorpholine, and MeOH for methanol. Other standard abbreviations can be identified by reference to *The Peptides, Analysis, Synthesis, Biology*, Vol. 1 and 2, ed. E. Gross and J. Meienhofer, Academic Press (New York 1987) and "IUPAC-IUB Commission on Biochemical Nomenclature", *J. Biol. Chem.*, 245:6489–6497 (1970) and *J. Biol. Chem.*, 250:3215–3216 (1975).

These examples illustrate the preferred methods for preparing the peptides of the invention. These examples are illustrative only and do not limit the scope of the invention.

EXAMPLE 1

Synthesis of Hexanoyl-Arg-Pro-Asp-NH-isobutyl

A. Preparation of N-isobutylaminomethyl resin

Merrifield resin (20 g, 1.06 mmol of Cl/g) was treated with isobutylamine (200 mL) at 45° C. for 72 hours. The flask was agitated by gentle rotation on a rotary evaporator at atmospheric pressure. After 72 hours, the excess isobutylamine was removed by filtration and the resin was washed with $CH_2Cl_2$ (3×100 mL), DMF (3×100 mL), $CH_2Cl_2$ (3×100 mL), MeOH (3×100 mL), $CH_2Cl_2$ (3×100 mL) and anhydrous ether (3×100 mL). The resulting resin was dried under reduced pressure (20.05 g).

B. Solid-Phase Synthesis of Hexanoyl-Arg-Pro-Asp-NH-isobutyl

The above mentioned peptide was synthesized by the solid-phase method via stepwise couplings. The synthesis was initiated with 3 mmol of N-isobutylaminomethyl resin (3 g, 1 mmol/g of resin). All the amino acids were protected at their α-amino group by a Boc group. A Tos group was used to protect the guanidino side chain of Arg. The side chain carboxyl group of Asp was protected by a Bzl group. All the couplings were done by the diisopropylcarbodiimide—HOBt method following the protocols given below:

| Step | Reagent | Time (minutes) |
|---|---|---|
| 1. | $CH_2Cl_2$ wash | 3 × 1 min |
| 2. | 40% TFA - 10% anisole in $CH_2Cl_2$ | 1 × 5 min |
| 3. | 40% TFA - 10% anisole in $CH_2Cl_2$ | 1 × 25 min |
| 4. | $CH_2Cl_2$ wash | 3 × 1 min |
| 5. | 10% NMM in $CH_2Cl_2$ | 2 × 5 min |
| 6. | $CH_2Cl_2$ wash | 3 × 1 min |
| 7. | DMF wash | 2 × 1 min |
| 8. | Boc-amino acid (9 mmol) and HOBt (3 mmol) in DMF | 1 × 3 min |
| 9. | DIC (9 mmol) added to the above and shaken | 1 × 180 min |
| 10. | Recouple, if necessary by repeating steps 4–9 | |
| 11. | DMF wash | 3 × 1 min |

Following the removal of N-terminal Boc-group of Arg and neutralization, the resulting peptide-resin was coupled with hexanoic acid (1.5 mL, 12 mmol) in the presence of HOBt (12 mmol) and DIC (12 mmol). The resin was then washed with DMF (3×50 mL) and CH$_2$Cl$_2$ (3×50 mL), and finally dried in a vacuum oven at 30° C. (4.46 g).

The peptide was cleaved from the resin support, in two batches (2.23 g/batch), by stirring in anhydrous liquid HF (45 mL), p-cresol (1.4 mL), p-thiocresol (1.4 mL), and dimethyl sulfide (1.4 mL) for 1 hour at 0° C. and three hours at 20° C. After removal of excess HF under reduced pressure, the resin-peptide mixture was extracted with anhydrous diethyl ether (3×200 mL). The ether extracts were discarded. The cleaved peptide was then extracted with 30% acetic acid (3×100 mL). After the removal of solvents under reduced pressure, the residue obtained was dissolved in water (60 mL) and freeze-dried (1.1 g). This solid was dissolved in 30% acetic acid (2×20 mL) and passed through an Amberlite IRA-68 (acetate form) ion exchange column (60 g, 1.6 meq/ml, 2.73 cm i.d.×18 cm length) in 30% acetic acid at a flow rate of 60 mL/hr. The appropriate fractions were combined and freeze-dried (930 mg).

The crude peptide was purified by preparative RP-HPLC using a Vydac 218TP1022 column (22×250 mm). The mobile phases employed were as shown below:

A=0.1% TFA/H$_2$O

B=0.1% TFA/CH$_3$CN—H$_2$O 4:1 v/v

A linear gradient of 5% B to 20% B over 60 minutes at a flow rate of 15 mL/min was used. The relevant fractions were combined and the solvents were removed under reduced pressure. The aqueous residue was freeze-dried to yield the final product (515 mg).

Thin layer chromatography (TLC) was performed on Merck F-254 silica plates (5×10 cm) in the following solvent systems (v/v):

Rf(1)=0.47 (1-BuOH:HOAc:H$_2$O, 4:1:1)

Rf(2)=0.68 (1-BuOH:HOAc:EtOAc:H$_2$O, 1:1:1:1)

Rf(3)=0.83 (1-BuOH:HOAc:Pyr:H$_2$O, 5:4:4:2)

Amino Acid Analysis (AAA): Arg 1.04 (1), Pro 1.00 (1), Asp 0.97 (1)

Liquid Chromatography—Mass Spectrometry (LC—MS) :[MH$^+$] at m/z=540 a.m.u. (Mol. Wt. 539.69), where MH$^+$ represents a positively charged mass ion; m/z is mass/charge; and a.m.u. is atomic mass units.

EXAMPLE 2

Synthesis of Acetyl-Arg-Pro-Asp-NH-isobutyl

The above peptide Acetyl-Arg-Pro-Asp-NH-isobutyl was synthesized by the solid-phase method described under Example 1. The protected amino acids were added sequentially to N-isobutylaminomethyl resin (3.4 g, 3.2 mmol). After the removal of N-terminal Boc-group of Arg and neutralization, the resulting peptide-resin was acetylated using acetic anhydride (8 mL) in CH$_2$Cl$_2$ (70 mL) containing 4-dimethylaminopyridine (120 mg) for 30 minutes. The resin was then washed with DMF (3×50 mL) and CH$_2$Cl$_2$ (3×50 mL), and finally dried in a vacuum oven at 30° C.

The peptide was cleaved from the solid support using liquid hydrogen fluoride and purified by RP-HPLC as described under Example 1.

TLC: Rf(1)=0.36, Rf(2)=0.62, Rf(3)=0.81

AAA: Arg 0.99 (1), Pro 0.97 (1), Asp 1.05 (1)

LC—MS: [MH$^+$] at m/z=484 a.m.u. (Mol. Wt. 483.57).

EXAMPLE 3

Solution-Phase Synthesis of Acetyl-Arg-Pro-Asp-NH-isobutyl

A. Boc-Asp(OBzl)-NH-isobutyl

To a solution of Boc-Asp(OBzl)-OH (6.46 g, 20 mmol) in ethyl acetate (70 mL) at −15° C., N-methylmorpholine (2.2 mL, 20 mmol) and isobutyl chloroformate (2.6 mL, 20 mmol) were added. After an activation time of 10 minutes at −15° C., isobutylamine (2.0 mL, 20 mmol) was added. The reaction mixture was stirred at −15° C. for 30 minutes and then allowed to warm to room temperature. After stirring for 2 hours at room temperature, the reaction mixture was quenched with a 5% sodium carbonate solution (100 mL). The two clear layers were transferred to a separatory funnel, and the organic layer was washed successively with 5% sodium carbonate solution (2×50 mL), water (3×50 mL), 5% citric acid (2×50 mL) and water (3×50 mL). The organic solution was dried over anhydrous sodium sulfate and concentrated under reduced pressure to afford a white solid. Yield 6.05 g (79.9% of theory).

B. HCl.Asp(OBzl)-NH-isobutyl

To a solution of Boc-Asp(OBzl)-NH-isobutyl (1.89 g, 5 mmol) in ethyl acetate (20 mL), 5N HCl—ethyl acetate (20 mL) was added. The solution was stirred for 40 minutes and concentrated under reduced pressure to give the product, HCl.Asp(OBzl)-NH-isobutyl as an oil. The product was dried in vacuum over KOH pellets overnight.

C. Z-Arg-Pro-Asp(OBzl)-NH-isobutyl

To a solution of Z-Arg(HCl)-Pro-OH (2.21 g, 5 mmol) in DMF (20 mL) at 0° C., 0.5 M HOBt/DMF (10 mL) and 0.5 M DCC/CH$_2$Cl$_2$ (10 mL) were added. After stirring for 30 min at 0° C., a solution of HCl.Asp(OBzl)-NH-isobutyl (1.57 g, 5 mmol) and NMM (1.1 mL, 10 mmol) in DMF (20 mL) were added. The reaction mixture was stirred at 0° C. for 2 hours and at room temperature overnight. The precipitated dicyclohexyl urea was filtered off and the filtrate was concentrated under reduced pressure to give the crude product Z-Arg-Pro-Asp(OBzl)-NH-isobutyl, as a solid (2.84 g, 84%).

D. Acetyl-Arg-Pro-Asp-NH-isobutyl

Z-Arg-Pro-Asp(OBzl)-NH-isobutyl (2.84 g) was dissolved in acetic acid (100 mL) and 10% Pd-C (2.7 g) was added. This solution was subjected to hydrogenation at 45 psi of hydrogen gas. The reaction was monitored by TLC, and after 24 hours the catalyst was filtered off. The solvent was removed under reduced pressure to give the product, Arg-Pro-Asp-NH-isobutyl, as an oil. This product was acetylated by dissolving in glacial acetic acid (10 mL) and treating with acetic anhydride in 5 portions (1 mL each time). After stirring for 4 hours, the reaction was quenched by the addition of water (5 mL) and the solvents removed under reduced pressure. The residue was dissolved in water (40 mL) and freeze-dried.

The crude peptide was purified by preparative RP-HPLC following the procedure described under Example 1. The product was lyophilized to constant weight (180 mg).

TLC: Rf(1)=0.36, Rf(2)=0.60, Rf(3)=0.70

AAA: Arg 0.99 (1), Pro 1.01 (1), Asp 1.01 (1)

LC—MS: [MH$^+$] at m/z=484 a.m.u. (Mol.Wt. 483.57).

EXAMPLE 4

Synthesis of Acetyl-Arg-Pro-Ala-NH-isobutyl

A. Acetyl-Arg-Pro-OH

Z-Arg(HCl)-Pro-OH (3 g, 6.79 mmol) was dissolved in glacial acetic acid (100 mL) and 10% Pd-C (1.5 g) was added. This solution was subjected to catalytic hydrogenation at 45 psi of hydrogen gas. The reaction was monitored by TLC, and after 48 hours the catalyst was filtered off. The solvent was removed under reduced pressure to give the product, Arg-Pro-OH as an oil. This was acetylated by dissolving in glacial acetic acid (10 mL) and treating with acetic anhydride in 3 portions (1 mL each time). After stirring for 3 hours, the reaction was quenched by the addition of water (2 mL) and the solvents removed under reduced pressure. The residue was dissolved in water (20 mL) and freeze-dried (2.2 g, 86.6% of theory).

B. Acetyl-Arg-Pro-Ala-NH-isobutyl

Boc-Ala-NH-isobutyl was prepared by coupling Boc-Ala-OH with isobutylamine following the procedure described in Example 3A. Boc-Ala-NH-isobutyl was deprotected using HCl-ethyl acetate and the hydrochloride salt of the peptide was dried in vacuum over KOH pellets overnight.

The coupling of Ac-Arg-Pro-OH with HCl.Ala-NH-isobutyl was accomplished following the procedure described under Example 3C. The crude product, Acetyl-Arg-Pro-Ala-NH-isobutyl was purified by preparative RP-HPLC and freeze-dried.

TLC: Rf(1)=0.42, Rf(2)=0.69, Rf(3)=0.81

AAA: Arg 1.03 (1), Pro 1.01 (1), Ala 0.96 (1)

LC—MS: [MH$^+$] at m/z=440 a.m.u. (Mol.Wt. 439.56).

EXAMPLE 5

Synthesis of Acetyl-Arg-Pro-Ser-NH-isobutyl

Boc-Ser(OBzl)-NH-isobutyl was prepared by coupling Boc-Ser(OBzl)-OH with isobutylamine, following the procedure described in Example 3A. This was deprotected using HCl-ethyl acetate and the hydrochloride salt of the peptide was dried in vacuum.

The coupling of Ac-Arg-Pro-OH with HCl.Ser(OBzl)-NH-isobutyl was accomplished following the procedure described under Example 3C. The protected tripeptide, Acetyl-Arg-Pro-Ser(OBzl)-NH-isobutyl was subjected to catalytic hydrogenation to remove the benzyl group, following the procedure described under 3D. The crude peptide, Acetyl-Arg-Pro-Ser-NH-isobutyl was purified by RP-HPLC.

TLC: Rf(1)=0.38, Rf(2)=0.40, Rf(3)=0.64

AAA: Arg 0.98 (1), Pro 1.02 (1). Under the conditions of peptide hydrolysis Ser underwent degradation and hence could not be detected.

LC—MS: [MH$^+$] at m/z=456 a.m.u. (Mol. Wt. 455.56).

EXAMPLE 6

Synthesis of Acetyl-Arg-Pro-Thr-NH-isobutyl

The peptide, Acetyl-Arg-Pro-Thr-NH-isobutyl, was synthesized as described in Example 5, with the substitution of Thr for Ser in position 3. The characteristics of the peptide are as follows:

TLC: Rf(1)=0.4, Rf(2)=0.64, Rf(3)=0.77

AAA: Arg 1.01 (1), Pro 0.99 (1). Under the conditions of peptide hydrolysis Thr underwent degradation and hence could not be detected.

LC—MS: [MH$^+$] at m/z=470 a.m.u. (Mol. Wt. 469.59).

EXAMPLE 7

Synthesis of Acetyl-Arg-Pro-Asp-NH-phenylethyl

Boc-Asp(OBzl)-NH-phenylethyl was prepared by coupling Boc-Asp(OBzl)-OH with phenylethyl amine, following the procedure described under Example 3A. This was deprotected using 4N HCl-dioxane and the hydrochloride salt of the peptide was dried in vacuum over NaOH pellets overnight.

The coupling of Acetyl-Arg-Pro-OH with HCl.Asp(OBzl)-NH-phenylethyl was accomplished following the procedure described under Example 3C. The protected tripeptide, Acetyl-Arg-Pro-Asp(OBzl)-NH-phenylethyl was subjected to catalytic hydrogenation to remove the benzyl group, following the procedure described under Example 3D. The crude peptide, Acetyl-Arg-Pro-Asp-NH-phenylethyl was purified by RP-HPLC.

TLC: Rf(1)=0.32, Rf(2)=0.60, Rf(3)=0.75

AAA: Arg 0.98 (1), Pro 1.01 (1), Asp 1.02 (1)

LC—MS: [MH$^+$] at m/z=532 a.m.u. (Mol. Wt. 531.62)

EXAMPLE 8

Neuromuscular Assay

This assay measures the ability of a peptide to affect the neuromuscular transmission. It is theorized that this ability is enabled by interaction of the peptide with the nicotinic acetylcholine receptor. Thymopoietin and thymopentin are known to have inhibitory effects upon neuromuscular transmission.

Various doses of the test peptide were dissolved in phosphate buffered saline and administered orally into female mice, weighing 25–30 grams (CD1 strain). The electromyographic assay was modified from the procedure according to G. Goldstein et al, *J. Neurol. Neurosurg. Psychiat.*, 31:453–459 (1968), in that the assay was performed 48 hours after administration of the peptide, rather than 24 hours as described in the paper. The mice were anaesthetized with 0.5 mL of a 10% urethane solution. The nerve was stimulated with a Grass S-48 stimulator and a Grass SIU-5A stimulus isolation unit (Grass medical instruments, Quincy, Me.) and the electromyographic response recorded with a Tektronix storage oscilloscope-5111 coupled to a 5A21N differential amplifier and a 5B10N time base (Tektronix, Beaverton, Oreg.).

With supramaximal nerve stimulation, at 30 impulses per second, the height of the tenth muscle action potential was expressed as a percentage of the first. P-values for testing statistical differences between the controls and the testing compounds were calculated by Dunnett's two-tailed t-test. The results obtained in the neuromuscular assay with the test peptide are presented in Table I below.

TABLE I

| Sequence | mg/kg | P value |
| --- | --- | --- |
| Acetyl-Arg—Pro—Asp—NH-isobutyl | 1 | 0.004 |
| | 1 | 0.000 |
| | 1 | 0.000 |
| | 0.1 | 0.000 |
| | 0.1 | 0.006 |
| Acetyl-Arg—Pro—Thr—NH-isobutyl | 1 | 0.000 |
| | 1 | 0.001 |
| Acetyl-Arg—Pro—Ser—NH-isobutyl | 1 | 0.000 |
| | 1 | 0.001 |
| Acetyl-Arg—Pro—Ala—NH-isobutyl | 1 | 0.001 |
| | 1 | 0.000 |
| Hexanoyl-Arg—Pro—Asp—NH-isobutyl | 0.1 | 0.000 |
| | 0.1 | 0.000 |
| Acetyl-Arg—Pro—Asp—NH-phenylethyl | 1 | 0.000 |
| | 1 | 0.001 |

EXAMPLE 9

Insulin Challenge Studies

Plasma concentrations of glucose are maintained at a physiological set point by a variety of neural and hormonal mechanisms. Insulin and glucagon derived from the pancreas are the principal hormones which lower and raise blood glucose levels, respectively. However, several additional hormones including growth hormone, epinephrine and adrenal glucocorticoids play important roles in glucoregulation. Deviations from the normal set point glucose concentrations are sensed by nerve cells residing within the hypothalamic region of the brain. Upon sensing a fall in blood glucose levels these cells activate poorly defined neural pathways in the brain resulting in the excitation of other hypothalamic cells which produce the 41-amino acid peptide corticotropin-releasing factor (CRF) and the 9-amino acid peptide arginine vasopressin (VP). These hypothalamic factors are secreted by the brain into a specialized hypothalamohypophysial portal capillary network and are carried by the blood in true endocrine fashion to the anterior lobe of the pituitary gland. In the anterior pituitary, these hormones bind with high affinity to receptors located on the corticotropic cells of the pituitary. Receptor activation by CRF and/or VP depolarizes the cells, increases calcium influx and increases the secretion of adrenocorticotropin (ACTH) into the peripheral blood. ACTH, as its name implies, stimulates the adrenal cortex to synthesize and release the primary glucocorticoid hormones, cortisol (in humans) and corticosterone (in rodents). These hormones subsequently act to increase plasma concentrations of glucose.

Thus, the administration of insulin to a normal subject, either human or rodent, can be used as a provocative challenge test to determine the subject's response to a stress. Stress, in this case, can be defined as the uncontrollable disruption of the subject's normal glucoregulatory mechanisms by exogenous insulin. Induction of such a stress experimentally is useful in determining the compensatory mechanisms involved in ameliorating stressful situations. Additionally, such a provocative challenge test is useful in determining the efficacy of pharmacological agents in modulating stress-induced endocrine changes and the disorders stemming from these changes.

A. Actions of Insulin on ACTH Secretion

To determine whether a drug can modify stress responses, the stress response itself must be characterized. To accomplish this goal, adult male Sprague-Dawley rats [Charles River, Kingston, N.Y.] were treated with increasing doses of insulin [Humulin, Eli Lilly Co.] ranging from 0.05 to 5 IU/kg or saline intraperitoneally after an overnight fast. Thirty minutes after administering insulin, the animals were sacrificed by decapitation and trunk blood was collected into polypropylene tubes containing 400 µl of 10% EDTA at 4° C. The plasma was separated by centrifugation and stored at −80° C. until being used for ACTH determinations. Plasma concentrations of ACTH were determined by radioimmunoassay using antiserum [IgG Corporation, Nashville, Tenn.] and $^{125}$I-labelled ACTH [ICN Corporation, Costa Mesa, Calif.] as described by Nicholson et al, *Clin. Chem.*, 30:259–265 (1984).

FIG. 1 shows the effects of insulin-induced hypoglycemia on the secretion of ACTH in male rats. The administration of saline vehicle ("0") did not affect basal levels of ACTH in the experimental animals (plasma ACTH levels— 42.1±4.2 pg/ml). At the lowest dose of insulin tested (0.05 IU/kg) ACTH levels were not elevated. At the 0.1 IU/kg dose, plasma ACTH concentrations were significantly greater than in vehicle treated controls and higher doses of insulin produced commensuratively greater ACTH responses which begin to plateau at the 5 IU/kg dose. Based on these data, a dose of 0.5 IU/kg was chosen for future experimental studies because it produced a high amplitude ACTH response which is easily detectable by RIA but is not a maximal response. If a higher dose of insulin were used, the plateau of the response is being approached which could make it difficult to detect any subsequent reversals of the stress effect induced by the insulin, whereas the dose of 0.5 IU/kg is on the steepest portion of the dose response curve making it easier to detect significant modifications in the ACTH secretory response.

B. Effect of a Peptide of the Invention on Insulin-Induced ACTH Secretion

As mentioned above, the administration of insulin can be used as a provocative challenge test to determine how an organism responds to stress and how the response can be manipulated. It was shown in FIG. 1 that, in rats, administration of insulin causes an increase in plasma concentrations of ACTH. The following experiment was conducted to demonstrate that this response could be manipulated by the peptides of this invention, for example, Acetyl-Arg-Pro-Asp-NH-isobutyl (hereafter "the peptide").

Adult male Sprague-Dawley rats were used in these experiments. After an overnight fast, the peptide or saline was administered by oral gavage or by subcutaneous injection to the experimental subjects. Doses of the peptide ranged from 0.1 to 10 mg/kg by the oral route and 0.03 to 3.0 mg/kg by the subcutaneous route. Forty-eight hours later all animals were treated with insulin (0.5 IU/kg) and were sacrificed by decapitation 30 minutes later. As above, trunk blood was collected in polypropylene tubes containing 400 µl of 10% EDTA at 4° C. Plasma was separated by centrifugation and stored at −80° C. until being used for ACTH determinations. ACTH concentrations were determined by RIA as described by Nicholson et al, cited above, using antiserum [IgG Corporation] and $^{125}$I-labelled ACTH [ICN Corporation].

The administration of 0.5 IU/kg of insulin intraperitoneally elevated plasma ACTH concentrations from 16.8±0.8 pg/ml to approximately 200 pg/ml in animals pretreated with saline by oral gavage or s.c. injection (FIG. 2). The administration of the peptide by the subcutaneous route at a dose of 0.1 mg/kg caused a slight suppression of the ACTH response to insulin. The threshold dose for significant suppression of insulin-induced ACTH secretion was 0.3 mg/kg s.c., when administered 48 hours before insulin. The peptide in subcutaneous doses of 1.0 and 3.0 mg/kg also suppressed the ACTH response. Administration of the peptide by oral gavage (p.o.) also suppressed the ACTH response to insulin. The peptide at 1 mg/kg p.o. had only minor effects on insulin-induced ACTH secretion. Higher doses of the peptide (3.0 and 10.0 mg/kg) caused highly significant decreases in the magnitude of the ACTH response to insulin.

Therefore, these experiments indicate that the peptide of the invention has the capability to suppress stress-induced ACTH secretion. It is apparent from FIG. 2 that the peptide administered by either the oral or subcutaneous route of administration is effective in this provocative challenge test. Furthermore, the minimal effective dose by the s.c. route of administration is ten-fold lower than the dose by the p.o. route suggesting that the gastrointestinal absorption barrier is traversed by the peptide.

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A tripeptide consisting of the formula $$R-X-Y-Z-NHR_1,$$

or a pharmaceutically acceptable acid- or base-addition salt thereof,
wherein

X is the D or L form of Arg;

R is H, a lower alkyl, or lower alkanoyl;

Y is a D or L form of Pro, dehydro-Pro, or hydroxy-Pro;

Z is a D or L form of an amino acid selected from Ser, Thr, Asp, Glu, Gln, Asn, beta-Asp, Val or Ile; and $R_1$ is selected from the group consisting of a straight chain or branched alkyl or alkenyl having 1 to 6 carbon atoms, optionally substituted with an aryl group or aryl substituted with either a halogen or a straight chain, a branched alkyl or alkenyl having 1 to 6 carbon atoms, or a cyclic methylene group of 3 to 7 carbon atoms.

2. A tripeptide selected from the group consisting of

Acetyl-Arg-Pro-Asp-isobutylamide,
Acetyl-Arg-Pro-Thr-isobutylamide,
Acetyl-Arg-Pro-Ser-isobutylamide,
Hexanoyl-Arg-Pro-Asp-isobutylamide,
Arg-Pro-Asp-methylamide,
Arg-Pro-Glu-isopropylamide,
Acetyl-Arg-Pro-Asp-methylamide,
Acetyl-Arg-Pro-Asp-isopropylamide,
Acetyl-Arg-Pro-Asp-phenylmethylamide,
Formyl-Arg-Pro-Asp-methylamide, and
Hexanoyl-Arg-Pro-Asp-methylamide.

3. A pharmaceutical composition comprising a therapeutically effective amount of at least one tripeptide consisting of the formula $$R-X-Y-Z-NHR_1,$$

or a pharmaceutically acceptable acid- or base-addition salt thereof,
wherein

X is a D or L form of Arg;

R is H, a lower alkyl, or lower alkanoyl;

Y is a D or L form of Pro, dehydro-Pro, or hydroxy-Pro;

Z is a D or L form of an amino acid selected from Ser, Thr, Asp, Glu, Gln, Asn, beta-Asp, Val or Ile; and $R_1$ is selected from the group consisting of a straight chain or branched alkyl or alkenyl having 1 to 6 carbon atoms, optionally substituted with an aryl group or aryl substituted with either a halogen or a straight chain, a branched alkyl or alkenyl having 1 to 6 carbon atoms, or a cyclic methylene group of 3 to 7 carbon atoms in a pharmaceutically acceptable formulation.

\* \* \* \* \*

UNITED STATES PATENT AND TRADEMARK OFFICE
CERTIFICATE OF CORRECTION

PATENT NO. : 5,639,729
DATED : June 17, 1997
INVENTOR(S) : Gideon Goldstein, Ponniah Shenbagamurthi, and James I. Koenig It is certified that error appears in the above-indentified patent and that said Letters Patent is hereby corrected as shown below:

Col. 10, line 31, delete "Me." and insert in place thereof -- MA --.

Signed and Sealed this

Eleventh Day of November, 1997

*Attest:*

BRUCE LEHMAN

*Attesting Officer*      Commissioner of Patents and Trademarks